United States Patent
Heilper et al.

(10) Patent No.: US 7,343,249 B2
(45) Date of Patent: Mar. 11, 2008

(54) VECTORIZATION OF SEQUENCE ALIGNMENT COMPUTATION USING DISTANCE MATRIX RESHAPING

(75) Inventors: Andre Heilper, Haifa (IL); Dmitry Markman, Acco (IL)

(73) Assignee: International Business Machines Corporational, Armonk, NY (US)

( * ) Notice: Subject to any disclaimer, the term of this patent is extended or adjusted under 35 U.S.C. 154(b) by 153 days.

(21) Appl. No.: 11/088,053

(22) Filed: Mar. 23, 2005

(65) Prior Publication Data

US 2006/0217892 A1 Sep. 28, 2006

(51) Int. Cl.
*G01N 33/48* (2006.01)
*G06G 7/48* (2006.01)
*C12Q 1/68* (2006.01)

(52) U.S. Cl. .............. 702/19; 702/20; 703/11; 536/23.1; 436/6

(58) Field of Classification Search ............ None
See application file for complete search history.

(56) References Cited

U.S. PATENT DOCUMENTS

| 4,384,273 A | 5/1983 | Ackland et al. |
| 4,509,187 A | 4/1985 | Ackland et al. |
| 4,905,143 A | 2/1990 | Takahashi et al. |
| 4,918,733 A | 4/1990 | Daugherty |
| 5,073,939 A | 12/1991 | Vensko et al. |
| 5,459,798 A | 10/1995 | Bailey et al. |
| 5,560,039 A | 9/1996 | Dulong |
| 5,757,959 A | 5/1998 | Lopresti |
| 2004/0024536 A1 | 2/2004 | Rognes |
| 2004/0049387 A1 | 3/2004 | Jeong et al. |
| 2004/0098203 A1 | 5/2004 | Rognes |

*Primary Examiner*—Shubo (Joe) Zhou

(57) ABSTRACT

A method for comparing data sequences includes accepting first and second data sequences of data elements. A distance matrix is computed. The matrix includes rows and columns of matrix elements, describing distances between the data elements of the first sequence and the data elements of the second data sequence. The distance matrix is reshaped by applying successive, incremental shifts to the rows or columns so as to produce a reshaped matrix. A best-score path through the reshaped matrix is calculated using vector operations, so as to quantify a similarity between the first and second data sequences.

1 Claim, 4 Drawing Sheets

VECTORIZATION OF SEQUENCE ALIGNMENT COMPUTATION USING DISTANCE MATRIX RESHAPING

FIELD OF THE INVENTION

The present invention relates generally to data sequence alignment, and particularly to methods and systems for computationally-efficient comparison of data sequences using vector operations.

BACKGROUND OF THE INVENTION

Dynamic Time Warping (DTW) is a well-known dynamic programming technique used for comparing and aligning sequences of data. Sequence alignment methods are described extensively in the literature, such as in a book by Sankoff and Kruskal entitled "Time Warps, String Edits and Macromolecules: the Theory and Practice of Sequence Comparison," Addison-Wesley Publishing Company, 1983, which is incorporated herein by reference. The authors describe different sequence matching techniques, including DTW, and their applications in a variety of fields. Applications range from computer science and mathematics, through DNA sequence matching in molecular biology, to voice recognition and even the study of bird song.

The terms DTW and sequence alignment are often used interchangeably in the literature. Typically, DTW refers to applications involving continuous data, such as voice recognition. Methods for aligning discrete data sequences (in which the data elements are selected from a discrete alphabet) such as DNA sequences, are often referred to as Levenshtein or Waterman-Smith methods.

The matrix computation involved in the various sequence alignment methods is sometimes implemented using systolic arrays. For example, U.S. Pat. No. 5,757,959, whose disclosure is incorporated herein by reference, describes a method for handwriting matching using a linear systolic array processor. The processor calculates an edit distance between an electronic handwritten pattern and a stored string.

Several methods for efficient sequence comparison are described in the patent literature. For example, U.S. Patent Application Publication 2004/0024536 A1, whose disclosure is incorporated herein by reference, describes a parallelization of the Smith-Waterman sequence alignment algorithm using parallel processing in the form of SIMD (Single-Instruction, Multiple-Data) technology. U.S. Patent Application Publication 2004/0098203 A1, whose disclosure is also incorporated herein by reference, describes a method for biological sequence alignment and database search. According to the described method, an optimal un-gapped alignment score of each diagonal in an alignment matrix is computed. A heuristic method for estimating a gapped alignment score is then employed. The estimate is used to identify a 1% fraction of the most interesting database sequences. These sequences are subsequently aligned with the query sequence using the Smith-Waterman method.

The methods described in the two patent application publications cited above have been implemented in a sequence database search tool called Paralign™, offered by Sencel™ Bioinformatics AS (Oslo, Norway).

SUMMARY OF THE INVENTION

Many applications of DTW and other sequence alignment methods process very long data sequences. A typical example is the matching of DNA chains in bioinformatics, in which the compared sequences often comprise thousands of elements. In order to find the best alignment between two data sequences, sequence alignment methods typically compute a distance matrix that defines distances between the elements of the two sequences. This matrix is the basis for calculating cumulative distances that correspond to different possible alignments between the two data sequences. The dimensions of the distance matrix are proportional to the length of the compared sequences. Thus, for applications that align long sequences, the distance matrix is a very large matrix.

In order to achieve reasonable computational complexity, it is desirable to vectorize the sequence alignment computation process. In other words, it is desirable to adapt the process to be performed using vector operations. Such vectorized processes can then be implemented using general-purpose vector processors or vector-oriented programming environments.

Distance matrices used in conventional sequence alignment methods, however, typically exhibit a "reverse-diagonal data dependency," as will be explained and demonstrated below. This data dependency property makes the alignment process difficult to vectorize. Systolic arrays that implement sequence alignment methods must typically use complex indexing schemes to cope with the reverse-diagonal data dependency of the matrix.

Embodiments of the present invention provide improved methods and systems for vectorizing the sequence alignment computation process. The disclosed methods apply a novel data reshaping process to the distance matrix to produce a reshaped distance matrix that does not exhibit reverse-diagonal data dependency. The reshaped matrix is then processed using a series of vector operations to find the best alignment between the two data sequences.

The inventors have implemented a vectorized DTW sequence alignment system using MATLAB™, in order to quantify the achievable computational complexity. The results indicate a reduction of computational complexity by a factor of 20-25, in comparison to a conventional DTW process.

There is therefore provided, in accordance with an embodiment of the present invention, a method for comparing data sequences, including:

accepting first and second data sequences including data elements;

computing a distance matrix including rows and columns of matrix elements that describe distances between the data elements of the first sequence and the data elements of the second data sequence;

reshaping the distance matrix by applying successive, incremental shifts to the rows or columns so as to produce a reshaped matrix; and calculating a best-score path through the reshaped matrix using vector operations, so as to quantify a similarity between the first and second data sequences.

In a disclosed embodiment, the first and second data sequences include DNA chains, the data elements represent types of DNA nucleotides, and calculating the best-score path includes evaluating a match between the DNA chains.

In another disclosed embodiment, calculating the best-score path includes applying a Dynamic Time Warping (DTW) process.

In yet another embodiment, the distance matrix possesses a reverse-diagonal data dependency, and reshaping the distance matrix includes eliminating the reverse-diagonal data dependency.

In still another embodiment, reshaping the distance matrix includes incrementing software pointers that point to locations in a memory, in which the rows or columns of the distance matrix are stored.

In a disclosed embodiment, reshaping the distance matrix and calculating the best-score path include applying a vector-processor.

In another embodiment, calculating the best-score path includes calculating, for at least a part of the matrix elements, respective cumulative distances along a path reaching the matrix elements, backward-reshaping the reshaped matrix, and extracting the best-score path from the backward-reshaped matrix responsively to the cumulative distances.

In yet another embodiment, calculating the best-score path includes performing calculations on the rows or the columns of the reshaped matrix. The calculations on the rows or the columns are respectively based, as a result of reshaping the distance matrix, on a prior calculation of only preceding rows or columns of the reshaped matrix.

There is also provided, in accordance with an embodiment of the present invention, apparatus for comparing data sequences, including:

an input device, which is coupled to accept first and second data sequences including data elements; and a processor, which is arranged to compute a distance matrix including rows and columns of matrix elements that describe distances between the data elements of the first sequence and the data elements of the second data sequence, to reshape the distance matrix by applying successive, incremental shifts to the rows or columns so as to produce a reshaped matrix, and to calculate a best-score path through the reshaped matrix using vector operations, so as to quantify a similarity between the first and second data sequences.

There is additionally provided, in accordance with an embodiment of the present invention, a computer software product for comparing data sequences, the product including a computer-readable medium, in which program instructions are stored, which instructions, when read by the computer, cause the computer to accept first and second data sequences including data elements, to compute a distance matrix including rows and columns of matrix elements that describe distances between the data elements of the first sequence and the data elements of the second data sequence, to reshape the distance matrix by applying successive, incremental shifts to the rows or columns so as to produce a reshaped matrix, to calculate a best-score path through the reshaped matrix using vector operations, so as to quantify a similarity between the first and second data sequences.

The present invention will be more fully understood from the following detailed description of the embodiments thereof, taken together with the drawings in which:

DETAILED DESCRIPTION OF EMBODIMENTS

System Description

Figure 1:
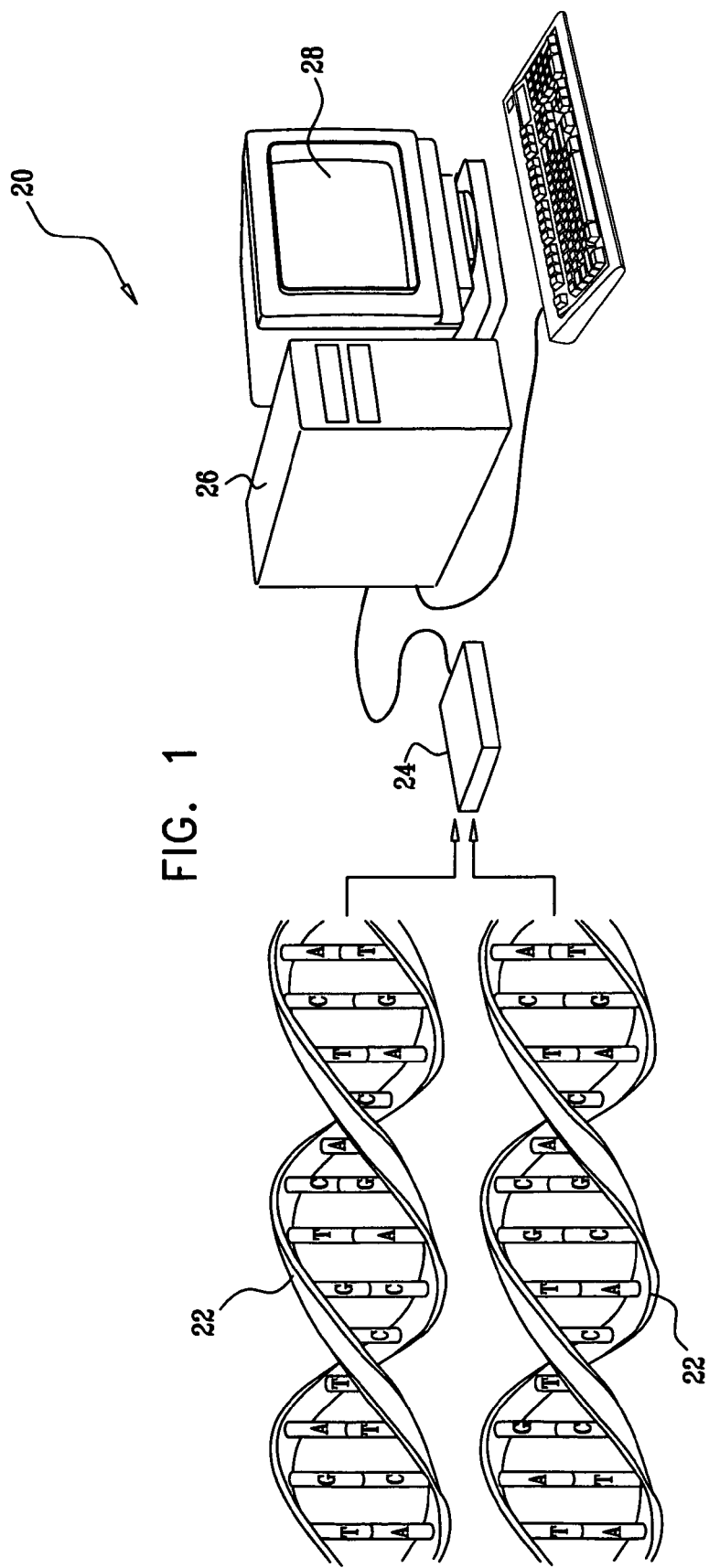
FIG. 1 is a diagram that schematically illustrates a system for sequence comparison, in accordance with an embodiment of the present invention.

FIG. 1 is a diagram that schematically illustrates a system 20 for comparing two data sequences 22, in accordance with an embodiment of the present invention. Sequences 22 comprise data elements, which can take different forms depending on the application of system 20. For example, in a system for matching DNA sequences, sequences 22 represent DNA chains, in which the data elements represent nucleotides in the chain. The data elements are selected from the alphabet {A, C, T, G} representing the four types of nucleotides that construct the DNA chain. Alternatively, in a voice recognition application, one of the sequences may represent a digitized voice signature. The second sequence may represent a digitized voice interval that is matched against the signature. The data elements in this example comprise digitized voice samples.

The two data sequences are input to system 20 using an input device 24. Input device 24 may comprise, for example, a communication line, an Internet connection, an interface to files stored on magnetic media, or any other suitable device for entering the two data sequences into system 20. In an alternative embodiment, only one data sequence 22 is accepted using input device 24. The second data sequence is taken from a corpus of data sequences, stored in a data structure (not shown) in system 20. For example, the comparison methods described below may be used in a database search application, wherein system 20 searches for the best match between an input data sequence and a database of stored sequences.

The two data sequences are compared by a processor 26, according to methods which will be described below. Typically, processor 26 finds the best alignment between the two data sequences. In the process of finding the best alignment, the processor also calculates a quantitative measure of the distance (or similarity) between the two sequences. The results of the comparison are subsequently provided to a user using an output device 28. The output device may comprise, for example, a computer monitor, a printer, a data file, a communication line, or any other suitable device for providing results to the user.

Typically, processor 26 comprises a general-purpose computer, which is programmed in software to carry out the functions described herein. The software may be downloaded to the computer in electronic form, over a network, for example, or it may alternatively be supplied to the computer on tangible media, such as CD-ROM. Further alternatively, processor 26 may be implemented in dedicated hardware logic, or using a combination of hardware and software elements. The processor may be a standalone unit, or it may alternatively be integrated with other computing equipment.

Additionally or alternatively, the processor may comprise a vector processor, which is particularly suitable for performing vector and matrix operations. For example, processor 26 may comprise an ALTIVEC™ vector processor, which is embedded in the core of a POWERPC™ processor, offered by Freescale Semiconductor, Inc. (Austin, Tex.).

Alternatively, the methods described hereinbelow may be implemented in software using software environments or languages that are particularly suitable for performing vector and matrix operations. For example, MATLAB™ offered by The Mathworks, Inc. (Natick, Mass.) may be used to implement the disclosed methods.

Data Sequence Alignment

As noted above, sequence comparison methods such as DTW typically find the best alignment between two data sequences, denoted $a_i$ and $b_j$, and calculate a quantitative measure of the distance (or the similarity) between them. In order to find the best alignment, these methods typically employ a distance matrix that defines distances between elements of the two data sequences.

Figure 2:
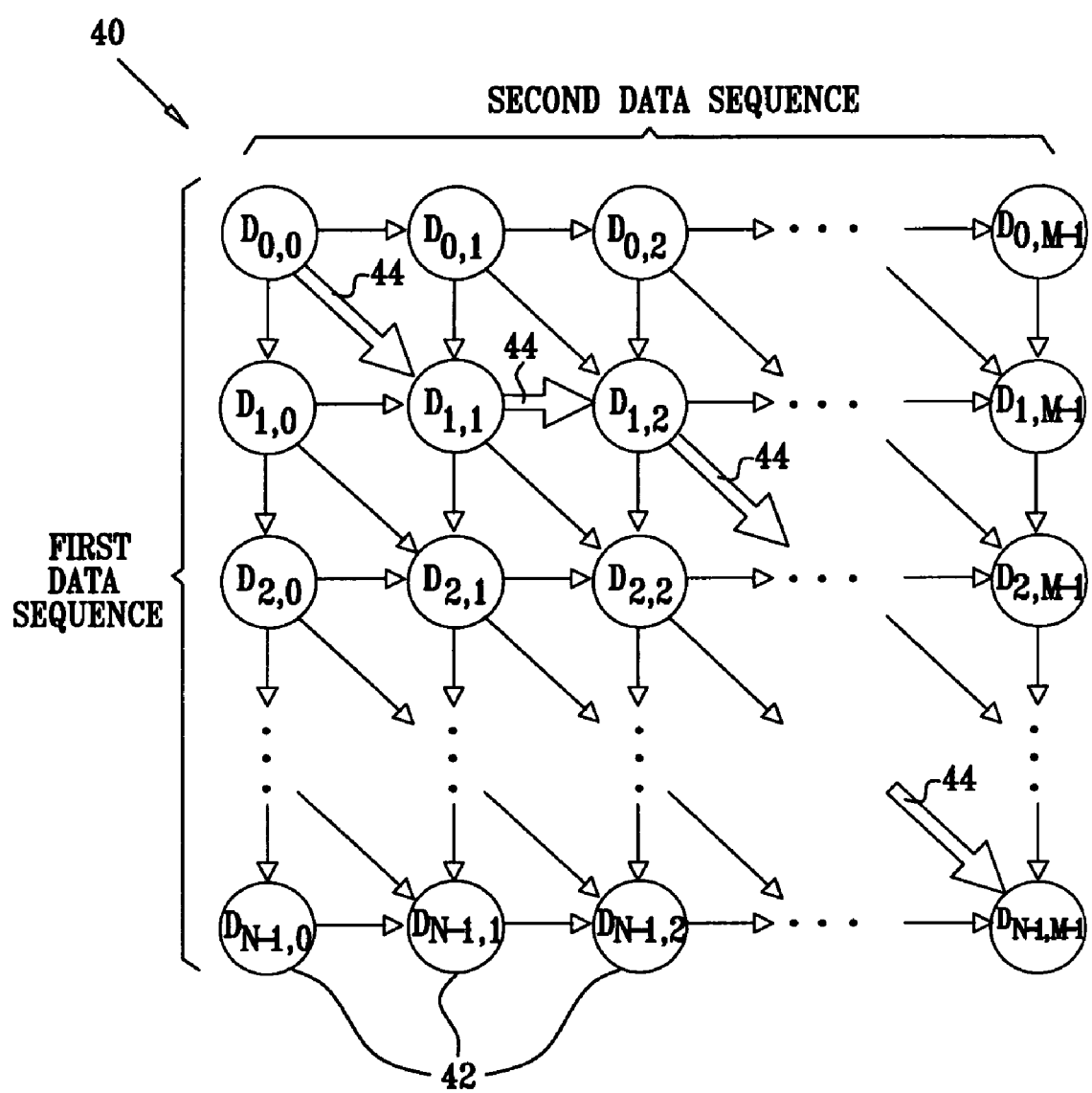
FIG. 2 is a diagram that schematically illustrates a distance matrix, in accordance with an embodiment of the present invention.

FIG. 2 is a diagram that schematically illustrates a distance matrix 40, in accordance with an embodiment of the present invention. Sequence $a_i$, whose length is denoted N, corresponds to the vertical axis of matrix 40. Sequence $b_j$, whose length is denoted M, corresponds to the horizontal axis of the matrix. Thus, distance matrix 40 is an N-by-M matrix. Matrix 40 comprises matrix elements 42, wherein each element 42 denoted $D_{i,j}$ represents the distance between the $i^{th}$ data element of sequence a (denoted $a_i$) and the $j^{th}$ data element of sequence b (denoted $b_j$). Here i=0 ... N−1 and j=0 ... M−1.

The values of elements 42 in matrix 40 are calculated according to a predefined distance function denoted dist($a_i$, $b_j$), which can take different forms depending on the application. For example, in a DNA matching application the distance function dist($a_i$,$b_j$) typically comprises a Boolean function that indicates whether or not the two data elements $a_i$ and $b_j$ represent the same nucleotide. In a voice recognition application or other signal processing application, the distance function may comprise an error function of the form dist($a_i$,$b_j$)=$(a_i-b_j)^2$. (The distance matrix is sometimes referred to as a cost matrix. In some implementations, the matrix contains similarity scores rather than distances. The matrix is then referred to as a similarity matrix.)

The different possible alignments between sequences ai and bj can be viewed as different paths through matrix 40. Matrix 40 can then be viewed as a directed graph, in which matrix elements 42 correspond to nodes. The possible transitions between nodes correspond to arcs. The possible node transitions through the distance matrix are marked with arrows in FIG. 2. Using this representation, each alignment between sequences a and b is described by a path through the directed graph, beginning at the top-left corner (denoted $D_{0,0}$) and terminating at the bottom-right corner (denoted $D_{N-1,M-1}$) of the matrix.

The distance between sequences ai and bj, given a particular alignment, is equal to the sum of matrix elements $D_{i,j}$ along the alignment path through the distance matrix. Therefore, finding the best sequence alignment is equivalent to finding a best-score path 44 through distance matrix 40, from top-left to bottom-right, that minimizes the cumulative sum of elements 42 along the path. For applications in which elements 42 comprise similarity scores rather than distances, best score path 44 is the path that maximizes the cumulative sum of similarity scores. In the description that follows, we will use distances as scores and a minimum-distance path as the best score path. Adaptation of the method to matrices using similarity scores is straightforward and is considered to be within the scope of the present invention. In the context of the present patent application and in the claims, both types of matrices are referred to collectively as "distance matrices," regardless of whether the matrix elements indicate distance or similarity.

Typically, sequence alignment methods known in the art find the best score path by scanning matrix 40 in a progressive manner. This progressive scan of the matrix calculates for each matrix element $D_{i,j}$ the minimum-distance path (and corresponding cumulative distance) from the top-left corner of the matrix up to the particular matrix element. When the progressive scan reaches $D_{N-1,M-1}$ (the bottom-right corner of the matrix), the minimum-distance path reaching this element represents the best alignment between sequence ai and bj. The cumulative distance of the minimum-distance path reaching element $D_{N-1,M-1}$ is equal to the distance between the two sequences, when aligned using the best alignment. Cumulative distances may be either stored in a corresponding cumulative distance matrix, denoted $CUMD_{i,j}$, or stored in-place in matrix 40.

Looking at the possible paths reaching each matrix element 42, it can be easily seen that the cumulative distance $CUMD_{i,j}$ of a particular element $D_{i,j}$ is a function of the cumulative distances of three adjacent elements. Namely, these elements are the element positioned one row above $D_{i,j}$, the element located one column to the left of $D_{i,j}$ and the element located one row above and one column to the left of $D_{i,j}$. Any path reaching element $D_{i,j}$ must pass through one of these three elements. Therefore, the minimum-distance path to element $D_{i,j}$ is the path that has the lowest cumulative distance out of these three paths. Formally, we can write:

$$CUMD_{i,j} = \min\{D_{i,j} + CUMD_{(i-1,j-1)}, D_{i,j} + CUMD_{(i-1,j)}, D_{i,j} + CUMD_{(i,j-1)}\}.$$

(When calculating CUMD values for elements located in the first row and/or the first column of matrix 40, some of the three adjacent CUMD values, corresponding to indices that fall outside the matrix, should be omitted.) Because of this recursive dependence, calculation of $CUMD_{i,j}$ requires the prior calculation of $CUMD_{(i-1,j-1)}$, $CUMD_{(i-1,j)}$ and $CUMD_{(i,j-1)}$. This dependence is commonly referred to as a "reverse-diagonal data dependency."

As noted above, practical implementations of sequence alignment methods often involve very long data sequences. Consequently, the implementation involves the processing of very large distance matrices. For example, DNA matching applications require the comparison of sequences having typical lengths ranging from a few hundreds to tens of thousands of elements. DTW is often selected as a sequence alignment method for such applications because of its reduced computational complexity. As is known in the art, DTW has a computational complexity of O(N.M), wherein N and M denote the lengths of the two data sequences and the dimensions of the distance matrix.

In order to reach reasonable computation time and complexity, it is often desired to implement DTW methods using vector operations and to parallelize the computation process to the maximum extent possible. Adapting the DTW method to comprise vector operations enables the use of powerful vector processors such as the ALTIVEC processor described above. However, the reverse-diagonal data dependency of the distance matrix makes the alignment computation difficult to vectorize. This dependence also makes the alignment computation difficult to implement using systolic arrays. The reverse-diagonal data dependency requires complicated indexing schemes and hence the use of specialized, non-standard systolic arrays.

The methods described below vectorize the DTW computation process. Vectorization is achieved by reshaping distance matrix 40 so as to remove the reverse-diagonal data dependency property.

Distance Matrix Reshaping

Figure 3:
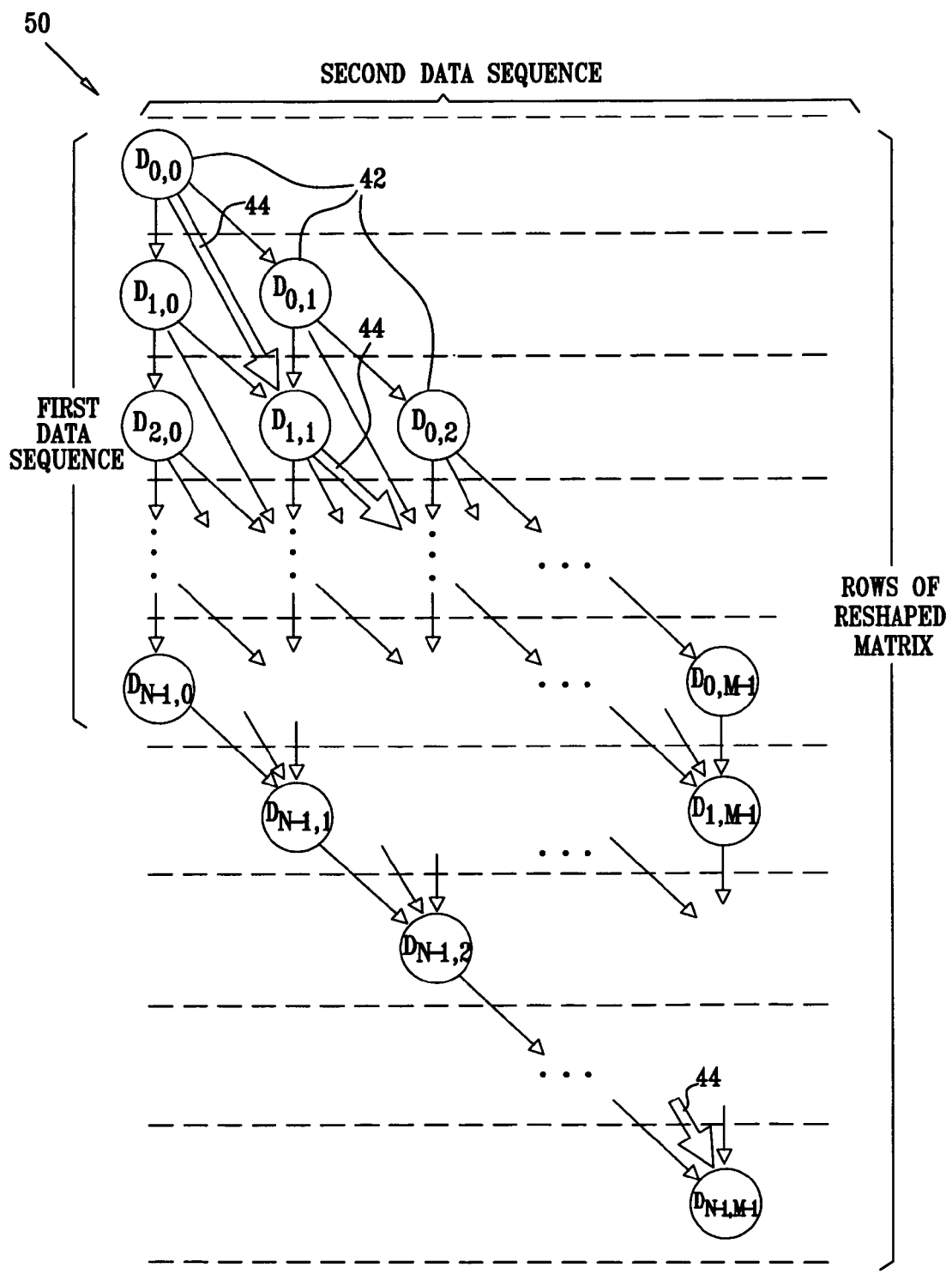
FIG. 3 is a diagram that schematically illustrates a reshaped distance matrix, in accordance with an embodiment of the present invention.

FIG. 3 is a diagram that schematically illustrates a reshaped distance matrix 50, in accordance with an embodiment of the present invention. Matrix 50 is derived from matrix 40 by applying a sequence of successive, incremental column shifts. The $j^{th}$ column (wherein j=0 . . . M−1) of matrix 40 is shifted by j positions down, to produce the respective column of matrix 50. The remaining elements of matrix 50, above and below the original columns of matrix 40, are unused and are typically set to zero. The resulting matrix 50 is an (N+M−1)-by-M matrix, which contains a reshaped replica of matrix 40 resembling a parallelogram.

The values of elements 42, the arrows connecting them, and minimum-distance path 44 remain unchanged when transforming matrix 40 into reshaped matrix 50. The only change is in the position, or indexing, of elements 42 in the matrix. While the reshaping process does not change the values of elements 42 and the relationships between them, the process does remove the reverse-diagonal data dependency property exhibited by matrix 40. Examining the reshaped matrix shown in FIG. 3, it can be seen that the cumulative distance $CUMD_{i,j}$ of each element $D_{i,j}$ in matrix 50 is still a function of three cumulative distances. However, in the reshaped configuration these three cumulative distances correspond to matrix elements that are located only in the two rows above element $D_{i,j}$. Specifically, the cumulative distance of element $D_{i,j}$ does not depend on any other element in row i or below it. Formally, the relation is given by:

$$CUMD_{i,j}=\min\{D_{i,j}+CUMD_{(i-2,j-1)}, D_{i,j}+CUMD_{(i-1,j-1)}, D_{i,j}+CUMD_{(i-1,j)}\}$$

The recursive dependence of cumulative distances in matrix 50 does not have any reverse-diagonal data dependency. As can be seen from examining the relation given above, the matrix of CUMD values can now be computed row by row. Each row in matrix 50 can be calculated using vector operations, assuming the two preceding rows have already been calculated. The simple and constant pattern of the data dependency in matrix 50 allows a conventional vector processor to perform the DTW computation in an efficient manner.

The reshaped configuration shown in FIG. 3 thus enables the calculation of the cumulative distances using vector operations. The following method demonstrates a vectorized DTW sequence alignment process that uses distance matrix reshaping.

Sequence Comparison Method

Figure 4:
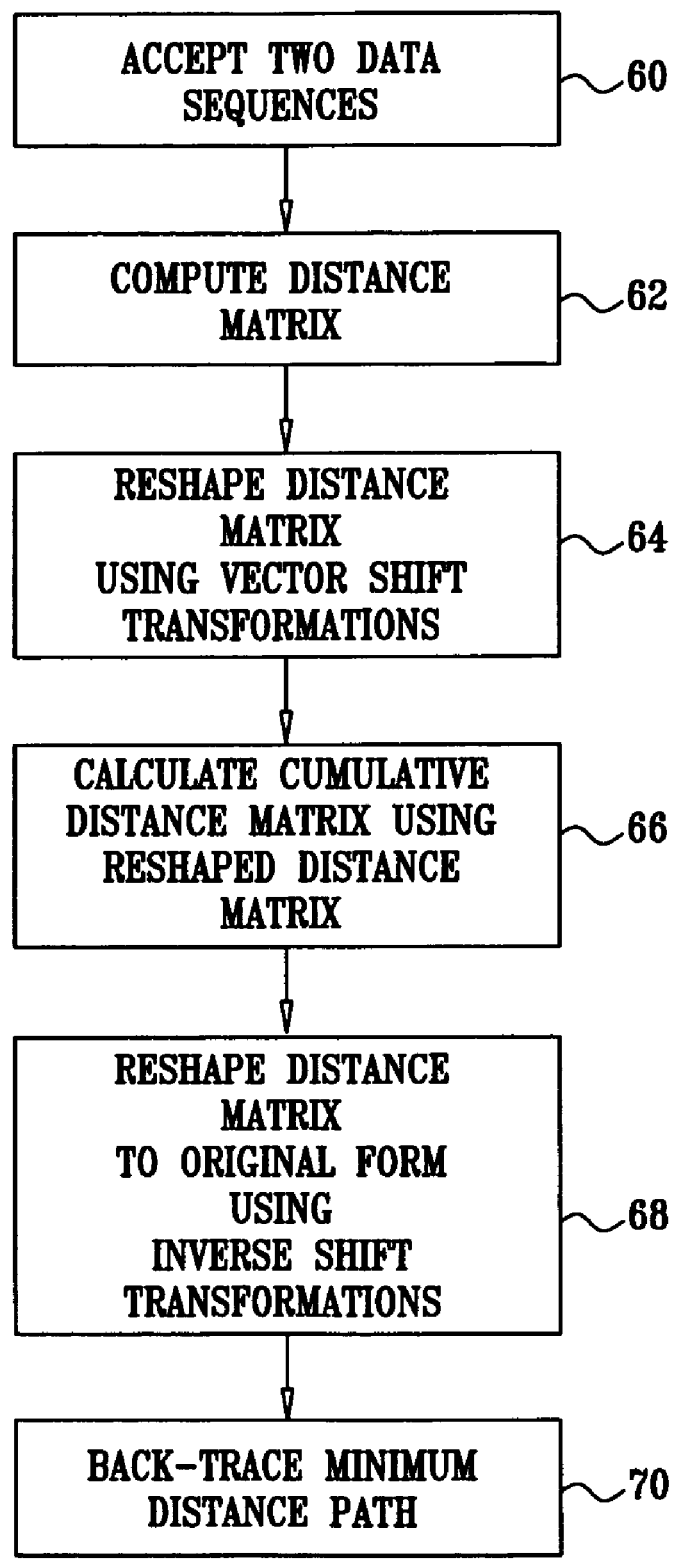
FIG. 4 is a flow chart that schematically illustrates a method for comparing data sequences, in accordance with an embodiment of the present invention.

FIG. 4 is a flow chart that schematically illustrates a method for comparing two data sequences, in accordance with an embodiment of the present invention. The method begins with processor 26 accepting, via input device 24, the two data sequences 22 denoted ai and bj, at a sequence acceptance step 60. Sequences ai and bj comprise N and M data elements, respectively. Processor 26 computes the N-by-M distance matrix 40, at a distance matrix computation step 62. Matrix 40 comprises matrix elements 42, denoted $D_{i,j}$, that describe distances between the data elements of sequences $a_i$ and $b_j$, according to a predefined distance function $dist(a_i,b_j)$. As noted above, the structure of the data sequences and the distance function depends on the specific application.

Having computed the distance matrix, the processor reshapes matrix 40 to produce reshaped matrix 50, at a reshaping step 64. The reshaped matrix has the configuration shown in FIG. 3 above. The reshaping process comprises a sequence of successive, incremental shift operations performed on the columns of matrix 40. The $j^{th}$ column (j=0 . . . M−1) of matrix 40 is shifted j positions down. Typically, shift operations are computationally lowcost and are readily supported in most hardware processors and software programming tools. For example, the ALTIVEC vector processor described above supports an inter-element vector instruction called "Vector Permute" (vperm). The vperm instruction accepts two input vector registers denoted vA and vB. Elements of these two vectors are copied into a destination vector register denoted vD, according to a permutation order specified by a third source vector register denoted vC.

In an alternative embodiment, instead of performing a series of column shifts, the reshaping process comprises an equivalent series of successive incremental row shifts. In this implementation, the ith row (i=0 . . . N−1) of matrix 40 is shifted i positions to the right, to produce a respective row of the reshaped matrix. This configuration similarly removes the reverse-diagonal data dependency of matrix 40. The calculation of cumulative distances is then performed column by column, instead of row by row.

In another embodiment, applying the sequence of successive, incremental shifts to the columns (or rows) of matrix 40 comprises incrementing software pointers that point to locations in a memory, in which matrix 40 is stored. Using this configuration, "virtual shifting" is performed without actually moving the matrix elements in the memory. Some vector processors, such as the ALTIVEC processor described above, support virtual shifting through "vector pointer" operations. Such virtual shifting may also be conveniently implemented in certain programming languages, such as C. This implementation reduces the computational complexity of the reshaping process.

In another disclosed embodiment, steps 62 and 64 may be combined. In this implementation the processor computes the distances between data elements of sequences ai and bj and stores them as matrix elements 42, already arranged in the reshaped configuration of matrix 50 of FIG. 3.

Having produced the reshaped distance matrix, the processor calculates a corresponding matrix of cumulative distances $CUMD_{i,j}$, at an alignment computation step 66. The processor calculates the CUMD values row by row. When calculating row i, rows i−1 and i−2 have already been calculated. Therefore, each $CUMD_{i,j}$ value can be readily calculated using the previously-calculated values of $CUMD_{(i-2,j-1)}$, $CUMD_{(i-1,j-1)}$ and $CUMD_{(i-1,j)}$. As noted above, this configuration exhibits no reverse-diagonal data dependency and is suitable for calculation using vector operations.

In some embodiments, processor 26 comprises a vector processor that processes vectors of length K. In these embodiments the vectorized computation is typically K times faster than a corresponding calculation that uses scalar operations. In applications involving relatively short sequences, wherein K≧M, the vector processor can calculate an entire row of matrix 50 simultaneously. In applications involving longer sequences, such that M>K, each row is typically divided into sections of size K for processing by the vector processor. Thus, the processor can handle sequences of any length, regardless of the maximum length vector supported by the processor.

There is some computational overhead associated with the parallelogram shape of matrix 50 and with the division of each row into sections of length K. However, this overhead is negligible in comparison to the savings in computational complexity achieved by the vectorization of the process.

Having completed the calculation of cumulative distances $CUMD_{i,j}$, the CUMD value of the bottom-right element of matrix 50 is equal to the distance between sequences $a_i$ and $b_j$. The corresponding minimum-distance path represents the best alignment that achieves this minimum distance. If all that is desired is the distance value between the sequences, and it is not necessary to perform the actual alignment, then the method can terminate here.

Otherwise, processor 26 reshapes matrix 50 and the CUMD matrix back to the original form of matrix 40, at a backward reshaping step 68. The processor performs an inverse series of shifts, compared to the series of shifts performed in reshaping step 64 above. Typically, the $j^{th}$ column (j=0 ... M-1) of matrix 50 is shifted j positions up, to reproduce the original distance matrix 40 and corresponding CUMD values. Backward reshaping step 68 is performed in order to simplify tracing back of the minimum distance path, which represents the best alignment between data sequences 22 $a_i$ and $b_j$. Similar to reshaping step 64 above, backward reshaping step 68 can be implemented by performing "virtual shifts" using pointer operations.

In an alternative embodiment, backward reshaping step 68 may be omitted from the method, at the expense of additional memory space that is required to store transition information during the process of finding the best-score path through matrix 50.

Finally, the processor traces back minimum distance path 44 from the reconstructed matrix 40, at a back-tracing step 70. The method terminates with processor 26 outputting the minimum distance path, representing the best alignment, and the corresponding minimum distance value to the user using output device 28.

Although the methods described hereinabove mainly address the vectorization of DTW computation, the same methods and principles may be used to vectorize other computation processes, and in particular other dynamic programming processes, in which a matrix exhibits reverse-diagonal data dependency.

Matlab Implementation Example

The following program code demonstrates a vectorized implementation of the disclosed method using the MATLAB environment described above. Using this MATLAB code, the inventors achieved a reduction of computation time by a factor of 20-25 in comparison to conventional, scalar DTW computation.

```
%------------------- vec_dtw.m --------------------------
function trace = vec_dtw(a,b)
UP = 2; LEFT = 3; LEFTUP = 1;
n = length(a); % assume m > n, otherwise swap between
                % a and b prior to function call
m = length(b);
[A,B] = meshgrid(b,a);
d_mat = dist_matrix(A,B); %calculates D_i,j;
trace_ind = zeros(n, m);
D = zeros(size(d_mat));
```

-continued

```
D(:,1) = cumsum(d_mat(:,1)); % calculate the first
                             % column of CUMD
D(1,:) = cumsum(d_mat(1,:)); % calculate the first row of CUMD
D(2:n,2:m) = d_mat(2:n,2:m); % D_i,j
CUMD = shift(D,Inf); % perform column-wise shift transform
trace_ind(2:n,1) = UP;
trace_ind(1,2:m) = LEFT;
trace_ind_new = shift(trace_ind,-1);
from = zeros(n+m-1,1);
to   = zeros(n+m-1,1);
for i = 3:n % prepare indices for row by row calculation
               % (relevant in software implementation only)
    from(i) = 2; to(i) = i-1;
end
for i = n+1:m
    from(i) = i-n+1; to(i) = i-1;
end
for i = m+1:m+n-1
    from(i) = i-n+1; to(i) = m;
end
% calculate the vector DTW of the shifted matrix row by row
% CUMD(i,j)=min{Dij+CUMD(i-1,j-1),Dij+CUMD(i-1,j),
%               Dij+CUMD(i,j-1)}, wherein D_i,j=dist(a(i),b(j)).
for i = 3:n+m-1
    [CUMD(i,from(i):to(i)), min_ind] = ... % Vectorization step
        min([CUMD(i,from(i):to(i))+CUMD(i-2,from(i)-1: to(i)-1); ...
% LeftUpper
            CUMD(i,from(i):to(i))+CUMD(i-1,from(i)   : to(i)); ...
% Upper
            CUMD(i,from(i):to(i))+CUMD(i-1,from(i)-1: to(i)-1)]);
% Left
    trace_ind_new(i,from(i):to(i)) = min_ind;
end
        % perform inverse shift transform for easy trace back (finding
        best alignment between the two sequences)
D = invshift(CUMD);
trace_ind = invshift(trace_ind_new);
trace = trace_back(trace_ind);
% Trace back procedure, returns the best alignment
% between the sequences.
function trace = trace_back(trace_ind)
UP = 2; LEFT = 3; LEFTUP = 1;
[n, m] = size(trace_ind);
% traceback
i = n; j = m;
trace = [i j];
while i>1 | j>1
    if      trace_ind(i,j) == UP
        i = i-1;
        trace = [trace; i j];
    elseif trace_ind(i,j) == LEFT
        j = j-1;
        trace = [trace; i j];
    else                  % LEFTUP
        i = i-1; j = j-1;
        trace = [trace; i j];
    end
end
trace = flipud(trace);
% ------------ Exemplary distance matrix --------------------
function res = dist_matrix(x, y) % calculate D_i,j - the distance
                                  % between a(i) and b(j)
res = abs (x-y);                  % The distance function is
                                  % problem specific
```

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method for comparing data sequences, comprising:

accepting first and second data sequences comprising respective first and second sets of data elements;

computing a distance matrix comprising rows and columns of matrix elements that describe distances between the data elements of the first data sequence and the data elements of the second data sequence, wherein the distance matrix possesses a reverse-diagonal data dependency;

converting the distance matrix into a reshaped distance matrix, whose rows or columns comprise incrementally-shifted replicas of respective rows or columns of the distance matrix, wherein converting the distance matrix into the reshaped distance matrix comprises eliminating the reverse-diagonal data dependency;

calculating a best-score path through the reshaped matrix using vector operations, so as to quantify a similarity between the first and second data sequences; and outputting an indication of the quantified similarity to a user.

* * * * *